United States Patent
Straub et al.

(10) Patent No.: US 8,071,824 B2
(45) Date of Patent: *Dec. 6, 2011

(54) METHOD FOR PRODUCING ALKENYLNITROBENZENE DERIVATIVES UNBRANCHED IN THE 1'-POSITION

(75) Inventors: Alexander Straub, Wuppertal (DE); Jörg Nico Greul, Leichlingen (DE); Norbert Lui, Odenthal (DE)

(73) Assignee: Bayer CropScience AG, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/373,255

(22) PCT Filed: Jul. 12, 2007

(86) PCT No.: PCT/EP2007/006178
§ 371 (c)(1),
(2), (4) Date: Nov. 5, 2009

(87) PCT Pub. No.: WO2008/006576
PCT Pub. Date: Jan. 17, 2008

(65) Prior Publication Data
US 2010/0076229 A1     Mar. 25, 2010

(30) Foreign Application Priority Data
Jul. 14, 2006   (DE) .......................... 10 2006 033 092

(51) Int. Cl.
*C07B 41/00* (2006.01)
*C07C 205/00* (2006.01)
(52) U.S. Cl. .................. 568/950; 568/705; 568/927
(58) Field of Classification Search ................... 568/927, 568/950, 705
See application file for complete search history.

(56) References Cited

FOREIGN PATENT DOCUMENTS

| EP | 0824099 A1 | 2/1998 |
|----|------------|--------|
| WO | 03074491 A1 | 9/2003 |
| WO | 2006061226 A1 | 6/2006 |

OTHER PUBLICATIONS

Bartoli, et al., "Conjugate addition of RMgX to nitroarenes. A very useful method of alkylation of aromatic nitro compounds," The Journal of Organic Chemistry 45: 522-524, American Chemical Society (1980).
Becker, H.G.O., et al., "General working instructions for catalytic reduction of aromatic nitro compounds," Organikum 15. Aufl.: 648-65, Deutscher Verlag der Wissenschaften (1976).
Lee, et al., "One-pot Pd-catalyzed hydrostannation/Stille reaction with acid chlorides as the electrophiles," Journal of Organometallic Chemistry 691: 1462-1465, Elsevier Science (2006).
Murata et al., "Mechanistic studies of intramolecular CH insertion reaction of arylnitrenes: isotope effect, configurational purity and radical clock studies," Journal of Physical Organic Chemistry 18: 9-20, John Wiley & Sons (2005).
Simmons, et al., "Cyclopropanes from Unsaturated Compounds, Methylene Iodide, and Zinc-Copper Couple," Organic Reactions 20: 1-131, John Wiley & Sons (1973).
Torii, et al., JP 62202091 A, Sep. 5, 1987, English Translation of abstract.
International Search Report for International (PCT) Application No. PCT/EP2007/006178, mailing date Oct. 31, 2007, WIPO, Geneva, Switzerland.
Copending U.S. Appl. No. 12/373,164, inventors Alexander Straub, et al., 371(c) Date of Nov. 5, 2009, United States Patent Office, Alexandria, VA (United States) (Not Published).

*Primary Examiner* — Jafar Parsa
(74) *Attorney, Agent, or Firm* — Sterne, Kessler, Goldstein & Fox P.L.L.C.

(57) ABSTRACT

The present invention relates to a process for preparing alkenylnitrobenzenes and alkylanilines, which are of significance as intermediates for fungicidally active alkylanilides.

9 Claims, No Drawings

METHOD FOR PRODUCING ALKENYLNITROBENZENE DERIVATIVES UNBRANCHED IN THE 1'-POSITION

The present invention relates to a process for preparing alkenylnitrobenzene derivatives which are of significance as intermediates for fungicidally active alkylanilides.

The prior art already discloses preparation methods for 1'-unbranched alkylanilines. Mention should be made of the Friedel-Crafts acylation of anilines with acid chlorides and subsequent reduction of the ketones formed (EP-A-824099), or the palladium-catalyzed reaction of bromoalkylbenzenes with benzophenone imine, or the copper-catalyzed reaction with ammonia, optionally followed by the elimination of the protecting group with hydroxylamine (WO-A-03074491 and WO-A-06061226).

Alkylnitrobenzenes can be converted to alkylanilines by reducing the nitro group and have been obtained to date, for example, by the nitration of alkylaromatics, as described in EP-A-824099 and WO-A-03074491, or by reaction of nitrobenzene derivatives with Grignard reagents, described in J. Org. Chem. 1980, 45, 522.

Nitro groups can, however, in the presence of Grignard reactions, give rise to various redox by-products.

JP-A-62-202091 describes the reaction of isobutyraldehyde with 2-nitrotoluene, which afforded only 2.2% 2-(2-nitrophenyl)-1-isopropylethanol.

J. Organomet. Chem. (2006), 691(8), 1462 describes the synthesis of 1-[3,3-dimethylbut-1-en-1-yl]-2-nitrobenzene proceeding from 2-nitrobenzoyl chloride. Owing to the high costs and the toxicity of the reagents used there, for example $Me_3SnF$, polymethylhydroxysiloxane and $Pd_2(dba)_3$, the method cannot be practised economically in an industrial process.

Consequently, the processes described in the prior art are too unselective, too complex and/or too costly.

It is thus an object of the invention to provide a process for preparing alkylnitrobenzenes, which does not have the disadvantages associated with the prior art.

It has now been found that, surprisingly, the reaction of 2-nitrotoluene with aldehydes such as pivalaldehyde or cyclopropylaldehyde proceeds in good yields.

The present invention therefore provides a process for preparing alkenylnitrobenzenes of the formula (I)

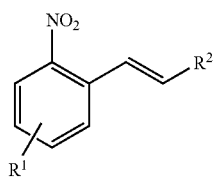

(I)

where $R^1$ is hydrogen, halogen, $-CR'(CF_3)_2$ where R' is selected from H, F and $O-C_{1-4}$-alkyl and is more preferably hydrogen, $R^2$ is cyclopropyl or t-butyl, comprising the steps of (i) reacting 2-nitrotoluenes of the formula (II)

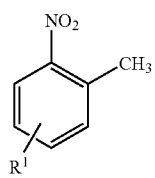

(II)

in which $R^1$ is as defined above with aldehydes of the formula (III)

$R^2-CHO$ (III)

in which $R^2$ is as defined above to give hydroxyalkylnitrobenzenes of the formula (IV);

(ii) converting the hydroxyalkylnitrobenzenes of the formula (IV) obtained from step (i)

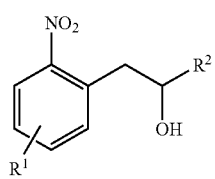

(IV)

in which $R^1$ and $R^2$ are each as defined above to haloalkylnitrobenzenes of the formula (V)

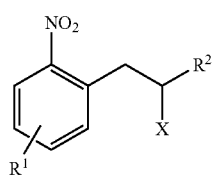

(V)

in which $R^1$ and $R^2$ are each as defined above and

X is a halogen atom or a leaving group such as tosylate (OTos), mesylate (OMes) or OSOCl, and (iii) subsequently eliminating the alkylnitrobenzenes of the formula (V) to give alkenylnitrobenzenes of the formula (I)

or (iv) directly eliminating the hydroxyalkylnitrobenzenes of the formula (IV) to give alkenylnitrobenzenes of the formula (I).

The present invention further provides the intermediates of the formula (I)

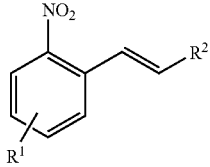

(I)

where
$R^1$ is halogen or —CR'(CF$_3$)$_2$ and R' is selected from H, F and O—C$_{1-4}$-alkyl and is more preferably hydrogen and
$R^2$ is t-butyl or cyclopropyl and
the substituent $R^1$ is preferably in the meta or para position, more preferably in the 4 position (para to the NO$_2$ group) of the aromatic;
of the formula (IV)

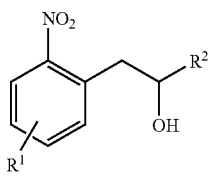

(IV)

where
$R^1$ is hydrogen, halogen, —CR'(CF$_3$)$_2$ and R' is selected from H, F and O—C$_{1-4}$-alkyl and is more preferably hydrogen and
$R^2$ is cyclopropyl or t-butyl and
the substituent $R^1$ is preferably in the meta or para position, more preferably in the 4 position (para to the NO$_2$ group) of the aromatic;
of the formula (VI)

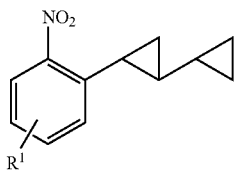

(VI)

where
$R^1$ is halogen, —CR'(CF$_3$)$_2$ and R' is selected from H, F and O—C$_{1-4}$-alkyl, and the substituent $R^1$ is preferably in the meta or para position, more preferably in the 4 position (para) of the aromatic;
and of the formula (V)

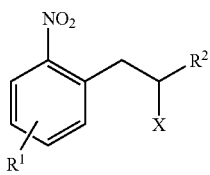

(V)

where
$R^1$ is hydrogen, halogen, —CR'(CF$_3$)$_2$ and R' is selected from H, F and O—C$_{1-4}$-alkyl and is more preferably hydrogen,
$R^2$ is cyclopropyl or t-butyl,
X is a halogen atom, preferably Cl or Br, or a leaving group, such as tosylate (OTos), mesylate (OMes) or OSOCl, and
the substituent $R^1$ is preferably in the meta or para position, more preferably in the 4 position (para) of the aromatic.

In connection with the present invention, the term "halogens" (X) encompasses elements which are selected from the group consisting of chlorine, bromine and iodine, preference being given to using chlorine and bromine.

Optionally substituted radicals may be mono- or polysubstituted, where the substituents may be the same or different in the case of polysubstitutions.

The definition "C$_1$-C$_4$-alkyl" encompasses the largest range for an alkyl radical defined herein. Specifically, this definition encompasses the meanings of methyl, ethyl, n-, isopropyl, n-, iso-, sec- and tert-butyl.

The inventive compounds can optionally be used as mixtures of different possible isomeric forms, especially of stereoisomers, for example E and Z, threo and erythro, and also optical isomers, and if appropriate also of tautomers. It is possible to use both the E and the Z isomers, and also the threo and erythro isomers, and also the optical isomers, any mixtures of these isomers, and also the possible tautomeric forms.

The process according to the invention can be illustrated by way of example by the following scheme (I):

(Scheme I)

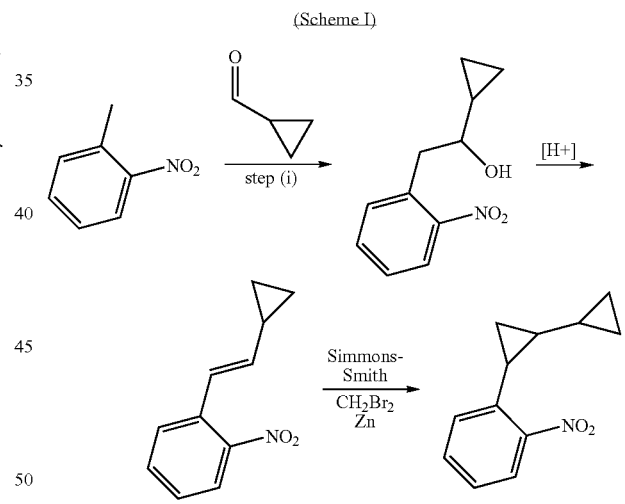

Step (i)

The inventive reaction of the 2-nitrotoluenes with the aldehydes in step (i) is effected preferably in the presence of a base.

Examples of useful bases include those which are selected from the group consisting of alkali metal and alkaline earth metal hydroxides, carbonates and hydrides, preference being given to using alkali metal hydroxides and particular preference to using NaOH or KOH.

Suitable solvents are all solvents which are inert under the existing reaction conditions, preference being given to using dimethylformamide (DMF), dimethylacetamide, N-methylpyrrolidone (NMP), dimethyl sulfoxide (DMSO) and dimethylenepropylurea (DMPU).

Steps (ii) and (iii)

In an alternative embodiment of the present invention, which will be illustrated in general terms by the following scheme II, the alcohol (IV) is first converted to a halide (V), for example a chloride, which is then eliminated to give the alkene (I):

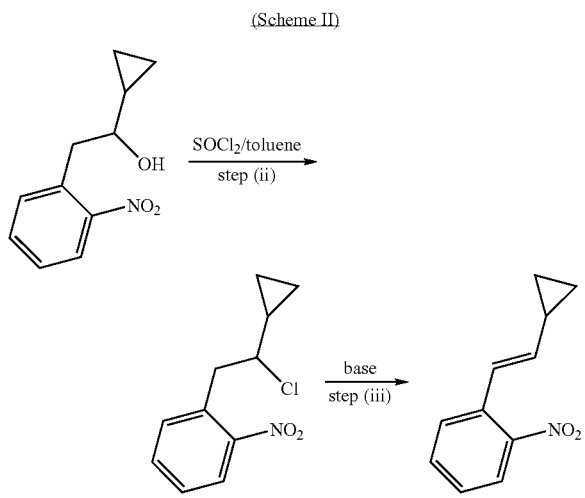

(Scheme II)

The halogenation of the alcohol (IV) to give the halide (V) in step (ii) is effected preferably with a halide former, which is selected from the group of the acid chlorides, such as thionyl chloride ($SOCl_2$), $POCl_3$, $COCl_2$ and $(COCl)_2$.

In a preferred embodiment of the invention, the haloalkylnitrobenzenes of the formula (V) are eliminated in step (iii) under base catalysis or thermally.

For the inventive base-catalyzed elimination step, bases are used which are, for example, selected from the group consisting of amines such as diethylamine, dipropylamine, diisopropylethylamine, dibutylamine, dicyclohexylamine, piperidine, triethylamine, tripropylamine, tributylamine, 1,8-diazabicyclo[5.4.0]undec-7-ene (DBU), 1,4-diazabicyclo[2.2.2]octane (DABCO); alkoxides such as sodium methoxide, potassium t-butoxide; alkali metal and alkaline earth metal hydroxides such as KOH, NaOH, LiOH, $Ca(OH)_2$; or carbonates such as soda, potash.

According to the invention, the base-catalyzed elimination is effected at standard pressure and temperatures in the range from −10 to 190° C., preferably from 0 to 140° C., more preferably from 10 to 100° C.

In a further embodiment of the invention, the elimination can also proceed thermally and spontaneously during the reaction with the halide former, as shown in the following scheme III:

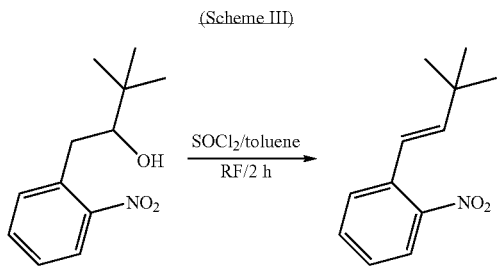

(Scheme III)

Step (iv)

In an alternative embodiment of the invention, the hydroxyalkylnitrobenzenes of the formula (IV) are eliminated directly in step (iv) under acid catalysis or thermally.

For the inventive acid-catalyzed elimination step, acids are used which are selected from the group consisting of mineral acids such as hydrochloric acid, sulfuric acid, phosphoric acid, acidic ion exchangers, organic acids such as methanesulfonic acid, benzenesulfonic acid, p-toluenesulfonic acid (PTSA), trifluoroacetic acid and acetic acid, particular preference being given to using p-toluenesulfonic acid and sulfuric acid.

According to the invention, the acid-catalyzed elimination is effected at standard pressure and temperatures in the range from 0 to 200° C., preferably from 20 to 150° C.

Both the acid-catalyzed and the thermal elimination reaction are effected preferably while simultaneously distilling off the water released in the reaction.

Alternatively, the reaction can be carried out in the presence of a water-binding agent, for example an acid anhydride such as acetic anhydride.

Suitable solvents for the elimination of water are, for example, selected from the group consisting of aromatics such as toluene, xylene, benzene, chlorobenzene, dichlorobenzene; aliphatics such as hexane, heptane, cyclohexane, methylcyclohexane and petroleum ether.

According to the invention, the thermal elimination is effected at standard pressure and temperatures in the range from 40 to 200° C., preferably from 50 to 150° C.

The 2-alkenylnitrobenzenes of the formula (I) thus obtained are valuable intermediates for the preparation of active agrochemical ingredients and can be converted by reduction to 2-alkylanilines.

Alternatively, they can also be converted to the corresponding cyclopropylnitrobenzenes by cyclopropanation.

According to the invention, the cyclopropanation is effected by Simmons-Smith reaction with dihalomethane and zinc and/or copper or diethylzinc. The reaction conditions of the cyclopropanation are known to those skilled in the art and have been described before in the prior art, for example in Org. React. 1973, 20, p. 1-131.

Alternatively, the cyclopropanation can also be effected by carbene addition with diazomethane.

In a further alternative embodiment of the invention, which will be illustrated by scheme (IV) below, the nitro group of the 2-hydroxyalkylnitrobenzenes is reduced to the amine.

The 2-hydroxyalkylanilines thus obtained can be eliminated and hydrogenated in a comparable manner.

The reaction conditions of the hydrogenation are known to those skilled in the art and have been described before in the prior art, for example in Becker, H. G. D. et al, Organikum (1976), Interdruck, Leipzig. Particular preference is given to hydrogenating in the liquid and/or gas phase in the presence of suitable hydrogenation catalysts. Suitable catalysts are especially Pd/C, $PtO_2$ and Raney nickel.

The hydrogenation is typically performed with hydrogen pressures of from 1 to 100 bar, preferably from 2 to 30 bar, more preferably from 5 to 10 bar, and at temperatures in the range from 0 to 150° C., preferably from 10 to 100° C. and more preferably from 15 to 50° C.

Alternatively, the hydrogenation can be effected with hydrogenating reagents which are selected from Zn, Fe, $SnCl_2$, Sn and dithionite.

The hydrogenation can be effected in the presence of an acid. Useful hydrogen sources also include formates and hydrazine.

(Scheme IV)

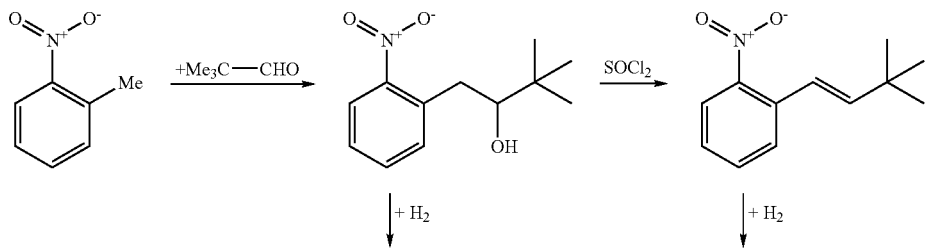

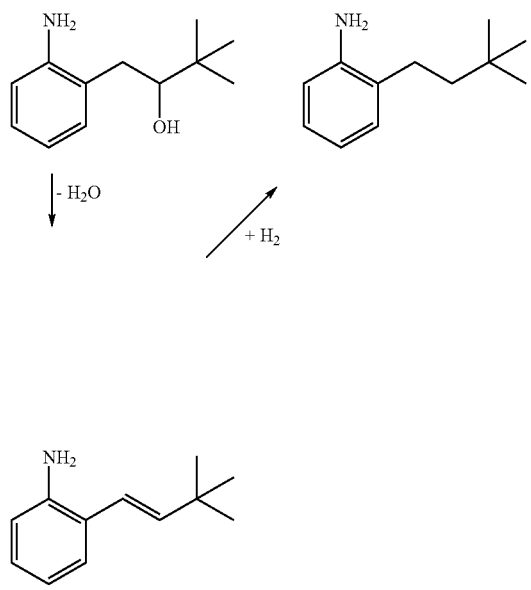

The examples which follow are intended to illustrate the subject matter of the invention in detail, but without restricting it thereto.

WORKING EXAMPLES

1-Cyclopropyl-2-(2-nitrophenyl)ethanol

To 4.9 g (35.7 mmol) of 2-nitrotoluene in 30 ml of DMF are added, within one hour, 0.168 g (2.55 mmol; 85% purity) of KOH and simultaneously 5 g (71.34 mmol) of cyclopropylcarboxaldehyde. The mixture is stirred at room temperature (RT) for 0.5 h, then 0.5 equivalent of cyclopropylcarboxaldehyde is added and the mixture is stirred at RT for a further hour. Subsequently, a majority of the DMF is distilled off under reduced pressure, and the residue is admixed with water and extracted with ethyl acetate. After the evaporation of the solvent and chromatography using silica gel (elution with toluene/ethyl acetate mixtures), 4.2 g (yield 55% of theory, purity (GC-MS 95.9%) of 1-cyclopropyl-2-(2-nitrophenyl)ethanol were obtained in the form of an oil.

$^1$H NMR (CDCl$_3$): 0.25-0.33 (2 m, 2H), 0.51-0.55 (2 m, 2H), 0.94-0.99 (m, 1H), 1.85 (broad s, 1H), 3.08-3.21 (2m, 2H), 3.36 (dd, 1H), 7.36 (t, 1H), 7.45 (d, 1H), 7.53 (t, 1H), 7.9 (d, 1H).

1-(2-Chloro-2-cyclopropylethyl)-2-nitrobenzene

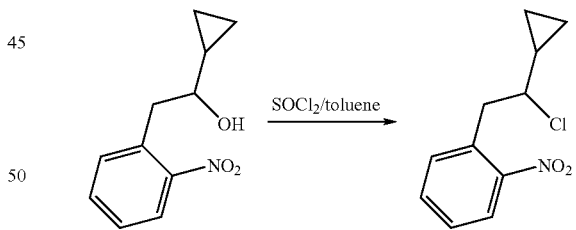

To 4 g (18.5 mmol; purity 96%) of 1-cyclopropyl-2-(2-nitrophenyl)ethanol in 50 ml of toluene are added, at room temperature, 2.3 g (19.5 mmol) of thionyl chloride, and then the mixture is stirred at 80° C. for 0.5 h. Then another 460 mg of thionyl chloride are added and the mixture is stirred at room temperature for a further 45 minutes.

After concentration under reduced pressure, dissolution in ethyl acetate and washing with saturated sodium bicarbonate solution, 3.5 g (80% of theory) of 1-(2-chloro-2-cyclopropylethyl)-2-nitrobenzene are obtained.

$^1$H NMR (400 MHz, d$^6$-DMSO): 0.32-0.38 (2 m, 2H), 0.87-0.92 (m, 2H), 0.58-0.63 (2 m, 2H), 1.23-1.26 (m, 1H), 3.38 (dd, 1H), 3.58 (dd, 1H), 3.6-3.7 (m, 1H), 7.54 (t, 1H), 7.55 (d, 1H), 7.65 (t, 1H), 7.98 (d, 1H).

Reaction of 2-nitrotoluene with pivalaldehyde

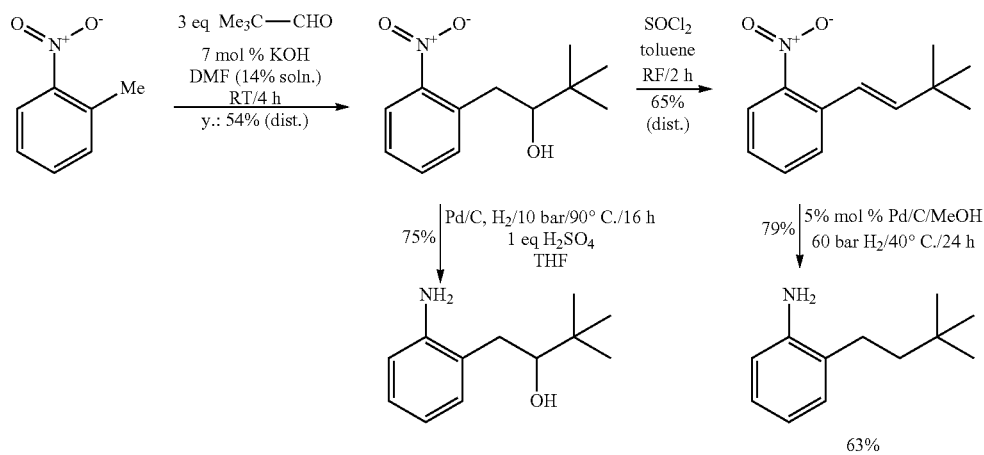

3,3-Dimethyl-1-(2-nitrophenyl)butan-2-ol

To 153.9 g (1.12 mol) of 2-nitrotoluene in 900 ml of DMF are added, within one hour, 4.5 g (80.2 mmol) of KOH and simultaneously 193.3 g (2.24 mol) of pivalaldehyde. Subsequently, first a further 0.5 equivalent of pivalaldehyde is added and the mixture is stirred at RT for one hour, then another 0.5 equivalent of pivalaldehyde is added and the mixture is stirred at room temperature for a further 2 hours. The mixture is acidified with 40 ml of 10 percent aqueous hydrochloric acid until the color changes (pH 4.5) and a majority of the DMF is distilled off under reduced pressure. After the residue has been distilled at 130° C./0.9 mbar, 136.8 g (yield 54% of theory, purity (GC-MS 98%) of 3,3-dimethyl-1-(2-nitrophenyl)butan-2-ol are obtained.

$^1$H NMR (CDCl$_3$): 1.01 (s, 9H), 1.8 (broad s, 1H), 2.81 (dd, 1H), 3.22 (d, 1H), 3.48 (d, 1H), 7.37 (t, 1H), 7.47 (d, 1H), 7.53 (t, 1H), 7.89 (d, 1H).

1-[3,3-Dimethylbut-1-en-1-yl]-2-nitrobenzene

To 40 g (179 mmol) of 3,3-dimethyl-1-(2-nitrophenyl)butan-2-ol in 400 ml of toluene at room temperature are added 23.44 g (197 mmol) of thionyl chloride, and the mixture is boiled under reflux for 2 h. After washing with 100 ml of saturated sodium bicarbonate solution and distilling the organic phase at 116° C./12 mbar, 20 g (48% of theory) of 1-[(1E)-3,3-dimethylbut-1-en-1-yl]-2-nitrobenzene are obtained.

$^1$H NMR (CDCl$_3$): 1.14 (s, 9H), 6.23 (d, 1H), 6.78 (d, 1H), 7.34 (t, 1H), 7.52 (t, 1H), 7.57 (d, 1H), 7.88 (d, 1H).

1-(2-Aminophenyl)-3,3-dimethylbutan-2-ol 3 g (13.4 mmol) of 3,3-dimethyl-1-(2-nitrophenyl)butan-2-ol are stirred in 50 ml of THF with 2.06 g of 65 percent sulfuric acid and 0.214 g of palladium/carbon (10%) at 90° C. under 10 bar of hydrogen pressure for 16 hours. Subsequently, the solution is filtered with suction through Celite and the filtrate is concentrated by rotary evaporation. After dissolution in ethyl acetate, washing with saturated sodium bicarbonate solution, and removal and concentration of the organic phase under reduced pressure, 2.2 g (75% of theory) of a solid are obtained. Purity (GC-MS): 88%.

MS (m/e): 193, 160, 136, 107 (100%).

2-(3,3-Dimethylbutyl)aniline 1 g (4.87 mmol) of 1-[3,3-dimethylbut-1-en-1-yl]-2-nitrobenzene are stirred in 20 ml of methanol with 0.26 g of palladium/carbon (10%) at 40° C. under 60 bar of hydrogen pressure for 24 hours. Subsequently, the solution is filtered with suction through Celite and the filtrate is concentrated by rotary evaporation. This gives 0.8 g (58% of theory) of an oil. Purity (GC-MS): 63%.

$^1$H NMR (CDCl$_3$): 0.99 (s, 9H), 1.5 (m, 2H), 2.45 (m, 2H), 3.6 (broad s, 2H), 6.67 (d, 1H), 6.68 (t, 1H), 7.01-7.05 (m, 2H).

1-[2-Cyclopropylvinyl]-2-nitrobenzene

To 1 g (4.25 mmol, purity 96%) of 1-(2-chloro-2-cyclopropylethyl)-2-nitrobenzene in 20 ml of dioxane is added 0.65 g (4.25 mmol) of 1,8-diazabicyclo(5.4.0)undec-7-ene, and the mixture is stirred at room temperature for 12 h. Subsequently, the solvent is concentrated under reduced pressure and the residue is admixed with ethyl acetate and water. After the organic phases have been removed and the solvent has been concentrated by evaporation, 0.7 g (79% of theory) of 1-[2-cyclopropylvinyl]-2-nitrobenzene is obtained.

$^1$H NMR (400 MHz, CDCl$_3$): 0.55-0.59 (m, 2H), 0.87-0.92 (m, 2H), 1.61-1.69 (m, 2H), 5.75 (dd, 1H), 6.94 (d, 1H), 7.3 (m, 1H), 7.47-7.57 (m, 2H), 7.86 (d, 1H).

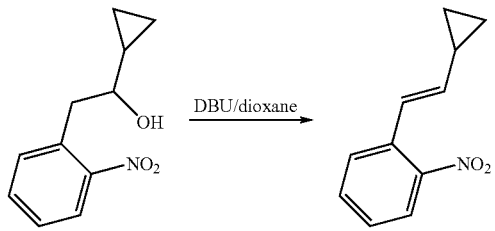

The invention claimed is:

1. An alkenylnitrobenzene of the formula (I)

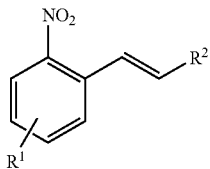 (I)

where
R$^1$ is halogen, or —CR'(CF$_3$)$_2$ and R' is selected from the group consisting of H, F and O—C$_{1-4}$-alkyl; and
R$^2$ is t-butyl or cyclopropyl.

2. An alkylnitrobenzene of the formula (VI)

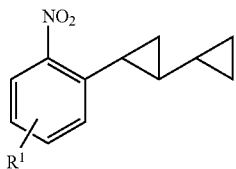 (VI)

where
R$^1$ is halogen, or —CR'(CF$_3$)$_2$ and R' is selected from the group consisting of H, F and O—C$_{1-4}$-alkyl.

3. A process for preparing the alkenylnitrobenzene of the formula (I) according to claim 1, the process comprising (i) reacting a 2-nitrotoluene of the formula (II)

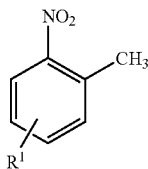 (II)

wherein R$^1$ is defined as in claim 1,
with an aldehyde of the formula (III)

R$^2$—CHO (III)

wherein R$^2$ is defined as in claim 1,
in the presence of a base to give a hydroxyalkylnitrobenzene of the formula (IV)

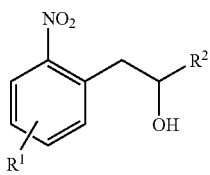 (IV)

in which
R$^1$ and R$^2$ are as defined above;

(ii) converting the hydroxyalkylnitrobenzene of the formula (IV) obtained from (i) to a compound of the formula (V)

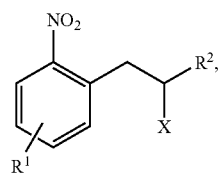 (V)

in which R$^1$ and R$^2$ are as defined above, and X is a halogen atom or a leaving group;
and (iii) eliminating HX from the compound of the formula (V) to give an alkenylnitrobenzene of the formula (I),
or (iv) eliminating H$_2$O from the hydroxyalkylnitrobenzene of the formula (IV) to give an alkenylnitrobenzene of the formula (I).

4. The process as claimed in claim 3, wherein the eliminating HX in (iii) is conducted under base catalysis or thermally.

5. The process as claimed in claim 3, wherein the eliminating H$_2$O in (iv) is conducted under acid catalysis or thermally.

6. The process according to claim 3, wherein the process comprises (i) reacting a 2-nitrotoluene of formula (II)

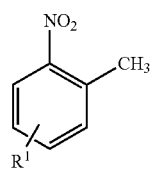 (II)

wherein R$^1$ is defined as in claim 3,
with an aldehyde of formula (III)

R$^2$—CHO (III)

wherein R$^2$ is defined as in claim 3,
in the presence of a base to give a hydroxyalkylnitrobenzene of formula (IV)

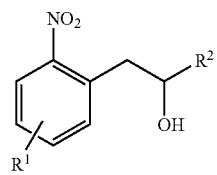 (IV)

wherein $R^1$ and $R^2$ are defined as in claim 3;
  (ii) converting the hydroxyalkylnitrobenzene of formula (IV) obtained in (i) to a compound of formula (V)

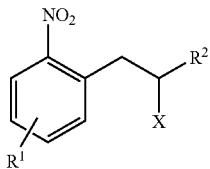
(V)

wherein
$R^1$ and $R^2$ are defined as in claim 3, and
X is a halogen atom or a leaving group;
and
  (iii) eliminating HX from the compound of formula (V) to give the alkenylnitrobenzene of formula (I).

7. The process of claim 6, wherein the eliminating HX in (iii) is conducted under base catalysis or thermally.

8. The process according to claim 3 comprising
(a) reacting a 2-nitrotoluene of formula (II)

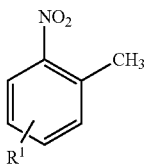
(II)

wherein $R^1$ is defined as in claim 5,
with an aldehyde of the formula (III)

$$R^2\text{—CHO} \qquad (III)$$

wherein $R^2$ is defined as in claim 5,
in the presence of a base to give a hydroxyalkylnitrobenzene of formula (IV)

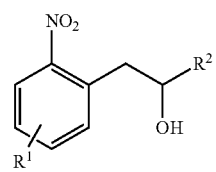
(IV)

wherein $R^1$ and $R^2$ are defined as in claim 3;

and
  (b) eliminating $H_2O$ from the hydroxyalkylnitrobenzene of formula (IV) to give the alkenylnitrobenzene of formula (I).

9. The process of claim 8, wherein the eliminating $H_2O$ in (b) is conducted under acid catalysis or thermally.

* * * * *